US012642980B2

(12) United States Patent     (10) Patent No.:   US 12,642,980 B2

English            (45) Date of Patent:     Jun. 2, 2026

(54) IMPLANTABLE MEDICAL DEVICE ELECTRONICS ENCAPSULANT

(71) Applicant: Cardiac Pacemakers, Inc., St. Paul, MN (US)

(72) Inventor: James Michael English, Cahir (IE)

(73) Assignee: Cardiac Pacemakers, Inc., St. Paul, MN (US)

( * ) Notice: Subject to any disclaimer, the term of this patent is extended or adjusted under 35 U.S.C. 154(b) by 226 days.

(21) Appl. No.: 18/420,432

(22) Filed: Jan. 23, 2024

(65) Prior Publication Data

US 2024/0245923 A1     Jul. 25, 2024

Related U.S. Application Data

(60) Provisional application No. 63/440,801, filed on Jan. 24, 2023.

(51) Int. Cl.
    *A61N 1/375*        (2006.01)

(52) U.S. Cl.
    CPC ................................. *A61N 1/3758* (2013.01)

(58) Field of Classification Search
    CPC ..................................................... A61N 1/3758
    See application file for complete search history.

(56) References Cited

U.S. PATENT DOCUMENTS

| | | | |
|---|---|---|---|
| 4,014,346 | A | 3/1977 | Brownlee et al. |
| 4,254,775 | A | 3/1981 | Langer |
| 4,314,562 | A | 2/1982 | Ware |

| | | | |
|---|---|---|---|
| 5,876,424 | A | 3/1999 | O'Phelan et al. |
| 5,999,398 | A | 12/1999 | Makl et al. |
| 6,031,710 | A | 2/2000 | Wolf et al. |
| 6,428,612 | B1 | 8/2002 | McPhilmy et al. |
| 6,603,654 | B2 | 8/2003 | Rorvick et al. |
| 6,881,516 | B2 | 4/2005 | Aamodt et al. |
| 7,194,309 | B2 | 3/2007 | Ostroff et al. |
| 7,263,401 | B2 | 8/2007 | Scott et al. |
| 7,485,277 | B1 | 2/2009 | Shepodd et al. |
| 7,769,457 | B2 | 8/2010 | Fonte |
| 7,968,226 | B2 | 6/2011 | Aamodt et al. |
| 8,065,006 | B2 | 11/2011 | Rorvick et al. |
| 8,065,007 | B2 | 11/2011 | Ries et al. |
| 8,463,393 | B2 | 6/2013 | Strother et al. |

(Continued)

FOREIGN PATENT DOCUMENTS

| | | |
|---|---|---|
| EP | 2934670 B1 | 1/2018 |
| WO | 2012036944 A1 | 3/2012 |

OTHER PUBLICATIONS

Henkel, Presentation, Macromelt Molding, 35 pages, https://www.ellsworth.com/globalassets/literature-library/manufacturer/henkel-loctite/henkel-presentation-technolmelt-formerly-branded-as-macromelt-molding.pdf Accessed Mar. 2, 2020.

(Continued)

*Primary Examiner* — Nathan T Leong

(74) *Attorney, Agent, or Firm* — Seager, Tufte & Wickhem LLP

(57) ABSTRACT

Implantable medical devices with a dampening layer, and methods for manufacturing such devices. A dampening layer may be dispensed onto assembled electrical components of an implantable medical device. The dampening layer may include a first material which is modified with a second material to reduce one or more of the heat capacity or density thereof.

14 Claims, 4 Drawing Sheets

(56)                    References Cited

U.S. PATENT DOCUMENTS

| | | |
|---|---|---|
| 8,774,921 B2 | 7/2014 | Fonte |
| 9,105,899 B2 | 8/2015 | Pakula et al. |
| 9,713,725 B2 | 7/2017 | Bobgan et al. |
| 10,040,021 B2 | 8/2018 | Ries et al. |
| 10,226,055 B2 | 3/2019 | Rothfuss et al. |
| 10,434,316 B2 | 10/2019 | Kelley et al. |
| 10,894,164 B2 | 1/2021 | Strommer et al. |
| 11,247,059 B2 | 2/2022 | Keller et al. |
| 2003/0204216 A1 | 10/2003 | Ries et al. |
| 2005/0245971 A1 | 11/2005 | Brockway et al. |
| 2009/0034769 A1* | 2/2009 | Darley ............... A61N 1/36038 |
| | | 381/328 |
| 2010/0305654 A1 | 12/2010 | Fonte |
| 2012/0069536 A1 | 3/2012 | Sporon-Fiedler et al. |
| 2013/0235550 A1 | 9/2013 | Stevenson et al. |
| 2015/0196867 A1 | 7/2015 | Ries et al. |
| 2015/0321013 A1 | 11/2015 | Smith et al. |
| 2016/0151635 A1 | 6/2016 | Frysz et al. |
| 2016/0287865 A1* | 10/2016 | Bobgan ............... A61N 1/3718 |
| 2018/0207427 A1 | 7/2018 | Webb et al. |
| 2019/0168005 A1 | 6/2019 | Li et al. |
| 2019/0321628 A1 | 10/2019 | Stevenson et al. |
| 2020/0054881 A1 | 2/2020 | Frustaci et al. |
| 2020/0121417 A1 | 4/2020 | Prescott et al. |
| 2020/0246625 A1 | 8/2020 | Stevenson et al. |
| 2020/0276440 A1 | 9/2020 | Stevenson et al. |
| 2021/0121705 A1 | 4/2021 | Ries et al. |
| 2022/0047876 A1* | 2/2022 | Becklund ........... A61N 1/37512 |
| 2022/0249852 A1 | 8/2022 | Peterson |
| 2022/0288401 A1 | 9/2022 | Landherr et al. |

OTHER PUBLICATIONS

International Search Report and Written Opinion dated Nov. 19, 2021 for International Application No. PCT/US2021/045724.

* cited by examiner

IMPLANTABLE MEDICAL DEVICE ELECTRONICS ENCAPSULANT

CROSS REFERENCE TO RELATED APPLICATIONS

The present application claims the benefit of and priority to U.S. Prov. Pat. App. No. 63/440,801, filed Jan. 24, 2023, titled IMPLANTABLE MEDICAL DEVICE ELECTRONICS ENCAPSULANT, the disclosure of which is incorporated herein by reference.

BACKGROUND

A wide variety of active implantable medical devices (AIMD) are known, including pacemakers, defibrillators, neural modulation systems, drug pumps, circulation systems, etc. Such devices often include an enclosure, often made of metal and hermetically sealed, which contain operational circuitry for the AIMD. The operational circuitry may be secured or fixed within the housing to prevent relative motion, which can cause damage to electrical interconnections and/or componentry. Prior approaches generally have used a frame and/or motion limiting inserts to hold the operational circuitry in desired positions. Electrical insulation between components has usually been provided by air gaps and selectively placed shielding. New and alternative solutions are desired.

OVERVIEW

The present inventors have recognized, among other things, that a problem to be solved is the need for new and/or alternative implantable medical device manufacturing methods and designs. In some examples, an implantable medical device is manufactured by placing electrical components inside at least a portion of the device housing, and selectively placing an encapsulant material or dampening layer over and/or around the components where desired. The dampening layer can act as a dielectric while also providing motion control. To limit the thermal effects on the component when the dampening layer is placed, the dampening layer or a portion thereof may include a filler material that reduces the heat capacity and/or thermal conductivity of the dampening layer. The dampening layer or encapsulant may also or instead be treated during placement, such as by injecting a gas to reduce heat capacity or thermal conductivity. In some examples, the filler material and/or injected gas also reduces the mass of the dampening layer, which in turn reduces the mass of the assembled implantable medical device.

A first illustrative and non-limiting example takes the form of a method of manufacturing an implantable medical device comprising assembling a plurality of electrical components for the implantable medical device; and dispensing a dampening layer onto a least a portion of the assembled electrical components, wherein the dampening layer comprises: a first material selected from the group consisting of thermoplastic, elastomer, thermoplastic elastomer (TPE), hot melt polymer and blends thereof, the first material having a first heat capacity; a second material having a second heat capacity that is less than the first heat capacity, the second material being selected from the group consisting of Zeolites, ceramic, carbon fibers, textile fibers, or entrapped gas; wherein the step of dispensing the dampening layer is performed by mixing the first and second materials together, and at least the first material is in a molten state when applied to the assembled electrical components.

Additionally or alternatively, the first material makes up a majority, by volume, of the dampening layer. Additionally or alternatively, the first material makes up a majority, by mass, of the dampening layer. Additionally or alternatively, the second material reduces a heat capacity of the dampening layer by at least 10%, relative to a heat capacity of the first material. Additionally or alternatively, the second material reduces a thermal conductivity of the dampening layer by at least 10%, relative to a thermal conductivity of the first material. Additionally or alternatively, the second material reduces a heat capacity of the dampening layer by at least 10%, relative to a heat capacity of the first material. Additionally or alternatively, the second material is entrapped gas, and the step of dispensing the dampening layer is performed by ejecting the first material from a foaming head. Additionally or alternatively, the dampening layer has a density that is reduced by at least 10% relative to a density of the first material.

Additionally or alternatively, the first material is provided in a pelletized form, the second material is mixed with the first material as a powder or pelletized form, and the mixed combination of the first and second materials is then heated to melt at least the first material so that the dispensing step can be performed. Additionally or alternatively, the method further comprises placing the electrical components in a first part of an enclosure for the implantable medical device prior to dispensing the dampening layer thereon. Additionally or alternatively, the method further comprises placing a second part of the enclosure after dispensing the dampening layer, and securing the first part and second part of the enclosure to one another.

Additionally or alternatively, the dispensing step is performed by molding the dampening layer onto the portion of the assembled electrical components. Additionally or alternatively, the second material second material is selected from the group consisting of Zeolites, ceramic, carbon fibers, and textile fibers, and the dispensing step further comprises infusing a gas into a blend of the first and second materials.

Additionally or alternatively, at least one electrical component is further surrounding by a separate layer of encapsulant having a different thermal conductivity than the dampening layer. Additionally or alternatively, at least one electrical component is further surrounding by a separate layer of encapsulant having a different heat capacity than the dampening layer.

Another illustrative and non-limiting example takes the form of an implantable medical device comprising: a plurality of electrical components; an hermetically sealed housing containing the electrical components; and a dampening layer securing the plurality of electrical components in the hermetically sealed housing, wherein the dampening layer comprises: a first material selected from the group consisting of thermoplastic, elastomer, thermoplastic elastomer (TPE), hot melt polymer and blends thereof, the first material having a first heat capacity; and a second material having a second heat capacity that is less than the first heat capacity, the second material being selected from the group consisting of Zeolites, ceramic, carbon fibers, textile fibers, or entrapped gas.

Additionally or alternatively, the first material makes up a majority, by volume, of the dampening layer. Additionally or alternatively, the first material makes up a majority, by mass, of the dampening layer. Additionally or alternatively, the second material reduces a heat capacity of the dampening layer by at least 10%, relative to a heat capacity of the first material. Additionally or alternatively, the second material reduces a thermal conductivity of the dampening layer by at least 10%, relative to a thermal conductivity of the first material. Additionally or alternatively, the second material reduces a heat capacity of the dampening layer by at least 10%, relative to a heat capacity of the first material. Additionally or alternatively, the second material is entrapped gas, wherein the dampening layer formed by ejecting the first material from a foaming head. Additionally or alternatively, the dampening layer has a density that is reduced by at least 10% relative to a density of the first material.

Additionally or alternatively, the second material second material is selected from the group consisting of Zeolites, ceramic, carbon fibers, and textile fibers, and the dampening layer further includes entrapped gas therein. Additionally or alternatively, the device further includes a component surrounding layer encapsulating or surrounding at least one of the electrical components and having a different thermal conductivity than the dampening layer.

This overview is intended to provide an introduction to the subject matter of the present patent application. It is not intended to provide an exclusive or exhaustive explanation. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
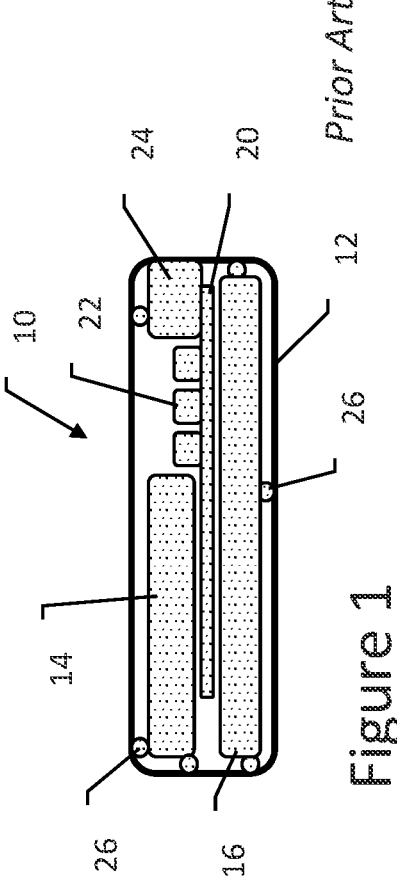
FIG. 1 shows a prior art implantable medical device in section view.

FIG. 1 shows an example prior art implantable medical device in a simplified section view. An implantable medical device 10 is shown in a simplified section view. The device 10 includes a housing 12 which is typically hermetically sealed, and may be made of any suitable material including metal, plastic, or other materials. Titanium is a commonly used material for housing 12. Inside the housing 12 are various components, shown illustratively as a battery 14, a capacitor 16, and a printed circuit board assembly (PCBA) 20 having a plurality of electric components 22 and coupled to a feedthrough assembly 24, which may be used for coupling the PCBA and components 22 to the outside of the device through a feedthrough, as is well known in the art. While not shown, housing 12 may include a header coupled to the feedthrough assembly 24 having a port or ports for receiving one or more leads.

The drawings herein generally correspond to an implantable defibrillator, which will have one or more relatively large capacitors 16; other implantable medical devices may have componentry of different types and relative sizes. The present invention may be used for any implantable medical device, particularly with active implantable medical devices (AIMDs). AIMDs may be, for example and without limitation, cardiac monitors, pacemakers, defibrillators, cardiac resynchronization therapy devices, cardiac assist devices neurostimulators, neuromodulators, spinal cord stimulators, Vagus nerve stimulators, deep brain stimulation systems, sacral nerve stimulators, or other systems. Some devices may store a therapeutic substance, such as a drug, if the AIMD is a drug pump, or insulin, if the AIMD is an insulin source. A reservoir for the therapeutic substance may be refillable, if desired. Circuitry for controlling and powering outputs may be provided on the PCBA 20.

The battery 14 may be a rechargeable battery, if desired, and associated charging circuitry may be provided. The battery may instead be primary cell. AIMDs typically also include communication circuitry, such as using the Medradio communication service or Bluetooth® communication, or other telemetry such as inductive telemetry, to communicate with an external "controller" or other external system such as a bedside monitor.

The components in the device 10 are held in position by a plurality of stabilizing features 26. The stabilizing features may be, for example and without limitation, polymeric dots, bars, rods, or an overall frame that holds the components in a desired position relative to the housing 12 and other components. The rest of the interior of the housing 12 is filled with gas/air. The gas/air provides thermal isolation between the components and the housing, as well as among the components. For example, if a processor is provided as one of the components 22, when that processor is active, convection will not provide much thermal transmission of heat to other components; generated heat may conduct via the PCBA 20 to some extent. The gas/air also serves as a dielectric, providing electrical isolation of the various components; if desired or needed, additional shielding may be provided, such as that shown in U.S. Pat. No. 9,713,725, the disclosure of which is incorporated herein by reference. The stabilizing features separate components 14, 16, 20, 22 from the housing 12 which, in some examples, may be thermally or electrically conductive, and also provides a degree of mechanical damping to the housing contents, as vibration of the electrical components can lead to various types of failure.

U.S. PG Pub. 2022/0047876, titled IMPLANTABLE MEDICAL DEVICE WITH RELATIVE MOTION CONTROL, the disclosure of which is incorporated herein by reference, describes an alternative to the use of a frame as shown in FIG. 1. Motion control inside the housing can be controlled by using a dampening layer which is selectively placed and/or molded over, around, and/or onto one or more components. However, the placement process presents additional challenges.

Figure 2:
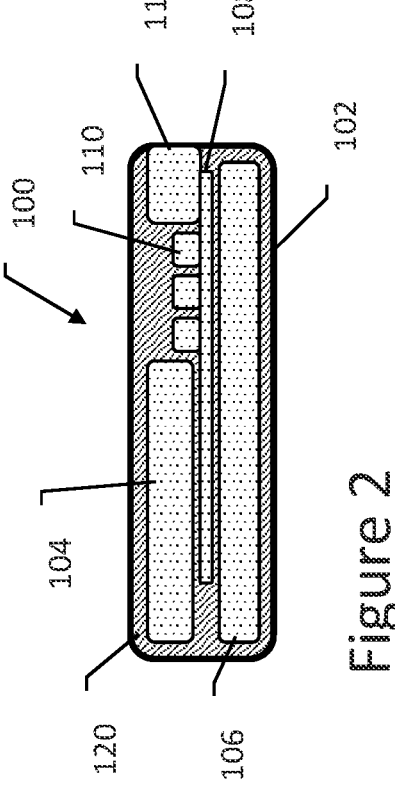
FIG. 2 shows an illustrative implantable medical device in a section view.

FIG. 2 shows an illustrative example of an implantable medical device with a motion dampening layer, in simplified section view. The device 100 includes a housing 102 containing operational circuitry including a battery 104, capacitor 106, and PCBA 108 that carries electronic components 110 and couples to a feedthrough assembly 112. Rather than using the stabilizing features 26 of FIG. 1, the device has a molded dampening layer 120. The dampening layer 120 may be placed around or over at least some components, or portions of some components, of the operational circuitry.

The dampening layer 120 may be a moldable and/or flowable material such as, but not limited to, a thermoplastic, elastomer, thermoplastic elastomer (TPE), hot melt polymer, or blends thereof. In some examples, the dampening layer 120 may be a composite or blend including two or more materials. By placing the dampening layer 120 on selected components, or all components, it can adhere to and provide positive fixation. In some examples, the dampening layer 120 can be dispensed with one or more, or all, of the components of the operational circuitry already placed in the housing, or within a first part of the housing. For example, the canister can be made of two halves, and the dispensing of dampening layer 120 can take place with the operational circuitry pre-assembled and electrically interconnected and placed in one half or part of the housing, such that housing, to some extent, serves to define a mold for the dampening layer. The second half or part of the housing may then be secured, such as by welding to the first half or part of the housing. In other examples, the housing may comprise a first part and a cap that attaches to the first part, wherein the first part defines most (such as 75% or more) of the housing itself; in an example, the housing may be a deep drawn or welded assembly. Alternatively, the dampening layer 120 may be dispensed with the operational circuitry held in a fixture, and the combined dampening layer and operational circuitry may then be placed in the housing or part of the housing.

One issue with the dispensing of the dampening layer 120 as just described is that some components may be thermally sensitive. To dispense, for example, a hot melt polymer, the material of the dampening layer may be heated to a relatively high temperature (60 C to 140 C, for example, depending on the material, or higher). Thus, during the dispensing step, the components of the operational circuitry would come into contact with the hot dampening layer material, and remain heated until the assembly cools. Such heating may cause damage to components, or increase aging of such components, or make such components more vulnerable to other types of damage. For example, a lithium chemistry battery containing a dielectric can form lithium crystals in response to temperature flux and if such crystals migrate to sensitive locations such as the battery header whether anode and cathode are accessible, such crystals could cause premature depletion of the battery by facilitating current flow or internal shorting. To address this heating issue, some examples mix the dampening layer material with a second material having a lower heat capacity, to reduce the heat impacts to the components of the operational circuitry.

In one example a dampening layer material is mixed with a ceramic material. The dampening layer material can be dispensed in a molten state, with the ceramic material suspended therein. Zeolite material may be used instead of the ceramic material. Thus, in an example, a first material, selected from the group of thermoplastic, elastomer, thermoplastic elastomer (TPE), hot melt polymer, or blends thereof, is mixed with a second material which is either a ceramic material or a Zeolite material. The mixing may take place while the first material is in pelletized form by adding a powdered or fibrous form of the second material in some examples. In other examples, the mixing may take place with the first material is in a molten state by mixing in a ceramic or Zeolite powder or fibers. The second material may instead be a carbon material or a textile material. Other mixing methods may be used as desired.

Ceramic materials may include, for example, Alumina (Al2O3), Boron nitride (BN) Magnesia (MgO), Aluminum nitride (AlN), Zirconia fiber powder (ZrO2), Zirconia powder (ZrO2), Boride, Boron, Carbides, Nitrides. Powdered ceramic material may include Alumina powder, Boron nitride powder, Magnesium oxide powder, Aluminum nitride powder, Zircon oxide powder. Grain size may be up to the hundreds of micrometers, thought typically less than one millimeter.

The second material may be selected for its relatively low heat capacity, compared to the first material. In an example, the first material may have a heat capacity that exceeds 1 J/g-° C., or exceeds 1.1 J/g-° C., or exceeds 1.2 J/g-° C., or exceeds 1.3 J/g-° C., and the second material has a heat capacity that is less than 1 J/g-° C., or less than 0.6 J/g-° C., or less than 0.4 J/g-° C. For example, the first material may be a TPE with heat capacity of about 1.3 J/g-° C. or more, and the second material may be a ceramic with a heat capacity of about 0.3 J/g-° C.

In another example, the first material may have a relatively higher thermal conductivity, and the second material has a relatively lower thermal conductivity. For example, the first material may have a thermal conductivity that exceeds 3 W/m-° C., or that exceeds 4 W/m-° C., or that exceeds 5 W/m-° C., and the second material has a thermal conductivity of less than 3 W/m-° C., or less than 2 W/m-° C., or less than 1 W/m-° C.

In another example, a second material may be mixed as part of the dispensing process. For example, a foaming head may be used in the dispensing step to mix and entrap a gas, such as air, dry air, nitrogen, etc. Doing so reduces the heat capacity of the dampening layer and also reduces the density of the dampening layer. In some examples, the second material is mixed with the first shortly before dispensing, so that the second material does not get heated to the same extent as the first.

In still another example, the first material may be mixed with the second material prior to dispensing, and a foaming head may be used during dispensing to entrap a gas as well, in which case the dampening layer may comprise first, second and third materials.

Several useful combinations are noted. In the following, the "Material A" may be selected from the group of thermoplastic, elastomer, thermoplastic elastomer (TPE), hot melt polymer, and/or blends thereof:

A blend of Material A, in an amount of 50% to 95% by weight, with a powdered ceramic material in an amount of 50% to 5% by weight, where powdered or granulated ceramic material is mixed into molten Material A.

A blend of Material A, in an amount of 50% to 95% by weight, with a powdered or granulated ceramic material in an amount of 50% to 5% by weight, where powdered ceramic material is mixed with the pelletized form of Material A prior to processing the pellets.

A blend as above by weight, but instead of ceramic material, powdered Zeolite, or Zeolite fiber, carbon fibers, or textile fibers.

Material A, or any of the above blends, combined with 5% to 35% by volume of a gas, where the gas is one or more of dry air, ambient air, nitrogen, or any of the Noble gasses.

Any of the above blends may be further modified by adding, by weight, up to 5% of a hydrogen getter or a desiccant material, as desired.

The inclusion of entrapped gas may have the additional benefit of reducing mass of the medical device, relative to the use of dampening layer that lacks such gasses. For example, the volume of some AIMDs, such as implantable pacemakers and defibrillators, generally is in the range of about 10 to about 60 cubic centimeters, or more or less, and has been reducing over time, with a mass in the range of 20 to 150 grams. The overall density of these systems is generally within a range of about 1.5 to about 2.5 grams per cubic centimeter, with many falling in a range of about 2 to about 2.3 grams per cubic centimeter. Even relatively recent large (first generation subcutaneous defibrillators) and small (leadless cardiac pacemakers and subcutaneous monitors) are in the same or similar density range. Higher densities, particularly relative to human tissue, can increase the risk of device migration. Adding entrapped gas has the additional benefit of reducing density, while also avoiding the introduction of a new material that could have an adverse chemical effect within the AIMD, and/or in the manufacturing (cleanroom) environment. Furthermore, entrapped gas reduces thermal conductivity, provides high dielectric strength, and does so without significantly increasing heat capacity.

In an example, the first material makes up a majority of the dampening layer by volume, for example, making up 51%, 60%, 70%, 75%, 80%, 85%, 90% or 95%, by volume, thereof. In an example, the first material makes up a majority, by weight or mass, of the dampening layer, making up 51%, 60%, 70%, 75%, 80%, 85%, 90%, 95%, 98%, or 99% thereof. If the second material is an entrapped gas, the first material may make up virtually all of the mass of the dampening layer, over 99% thereof.

In an example, the second material reduces a heat capacity of the dampening layer by at least 10%, relative to a heat capacity of the first material. For example, if the first material is TPE with a heat capacity of about 1.3 J/g-° C., and the second material is dry air, with a heat capacity of about 1.0 J/g-° C., the dry air would, in essence, count as having zero heat capacity given the mass of dry air that could be entrapped is quite low. Using a foaming head and providing dry air at a volumetric ratio of about 20% dry air to 80% of TPE would reduce the heat capacity of the dampening layer by more than 10%. The heat capacity may be reduced instead by 15%, or 20%, or 25%, or 30%, or 35%, or 40%, or 45%, or 50%, or more. A blend of a first material, such as TPE, with a second material, such as a ceramic powder or ceramic granules, at a ratio of 2:1 TPE to ceramic by mass, and then foaming to a volumetric ratio of about 30% air to 70% of the blend may in combination, reduce the heat capacity of the dampening layer by more than 50%.

In an example, the second material reduces a thermal conductivity of the dampening layer by at least 10%, relative to a thermal conductivity of the first material. Again, the mass and/or volumetric ratio may drive such an example. If the first material has a thermal conductivity of about 4 W/m-° C., and the second material has a thermal conductivity of less than 1 W/m-° C., a blend in a 3:1 ratio would reduce the thermal conductivity by close to 20%. The thermal conductivity may be reduced instead by 15%, or 20%, or 25%, or 30%, or 35%, or 40%, or 45%, or 50%, or more.

In an example, the second material reduces the density of the dampening layer by about 10%, or 15%, or 20%, or 25%, or 30%, or 35%, or 40%, or 45%, or 50%, or more. For example, using entrapped dry air, a ratio of about 3:1 of the first material to the dry air, by volume, would reduce the resulting density by about 25%.

Figure 3:
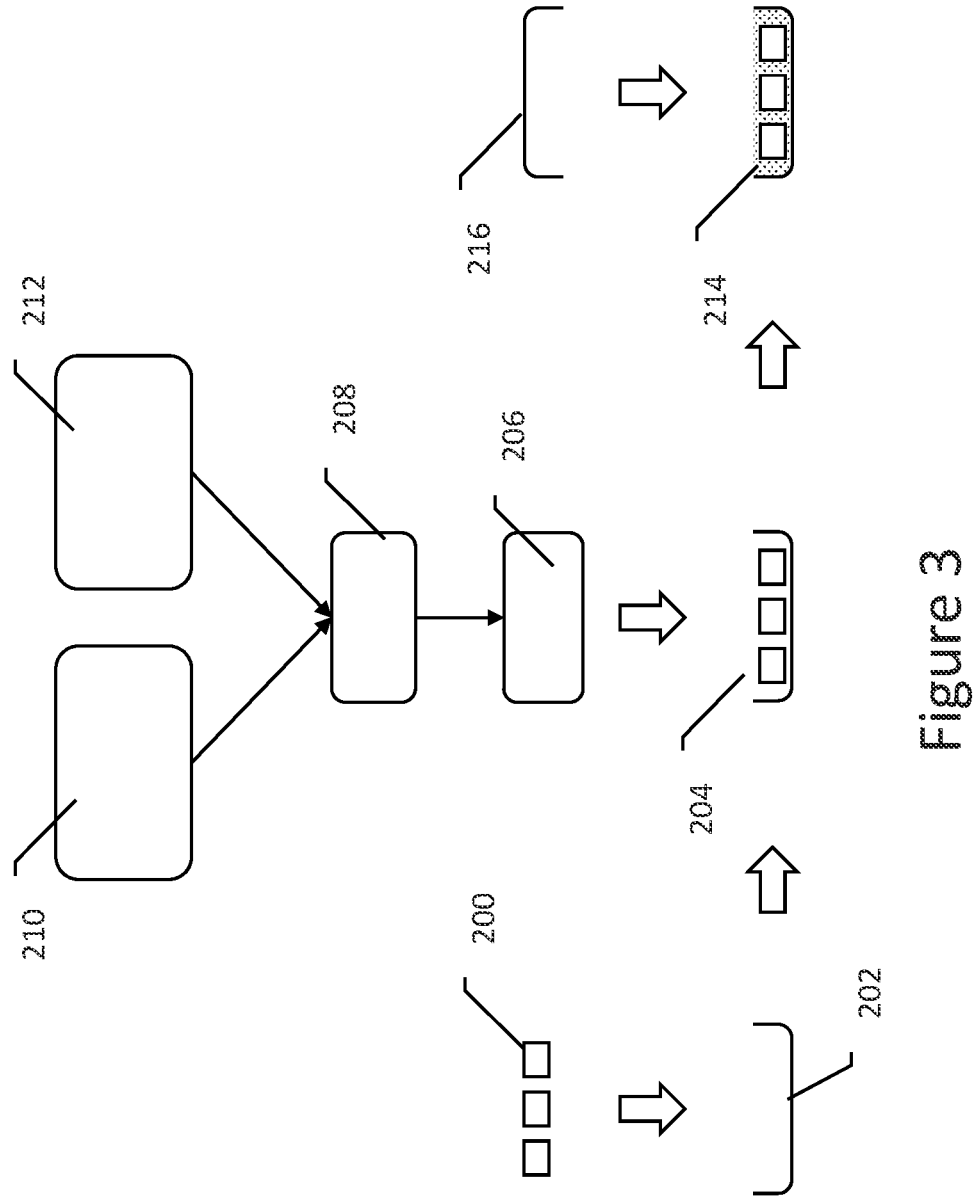
FIG. 3 shows in simplified form a device manufacturing system.

FIG. 3 shows an illustrative manufacturing method, in a highly simplified form. Starting on the left, an electronics assembly 200 is placed in an AIMD housing 202. The electronics assembly 200 may be, for example, an assembly of a circuit board and circuit board mounted components, along with a battery, capacitor or other operational circuitry componentry. The electronics assembly may include, for example, and without limitation, one or more low power hybrid assemblies, (optionally) one or more high power hybrid assembly, application specific integrated circuits (ASIC), including optionally any of digital ASIC, analog ASIC, and/or mixed signal ASIC, gate arrays, (such as a field programmable gate array), logic circuits, operational amplifiers, discrete components and chips of any desired type, microprocessors, microcontrollers, memory, oscillators, etc.

The electronics assembly 200 may be partly or wholly assembled separately, or may be assembled in whole or in part after placement in the AIMD housing 202. The AIMD housing 202 may be a first housing part, such as a canister half, as shown, though other configurations may be used instead. In some examples, the placement of the electronics assembly 200 into AIMD housing 202 may include electrically linking electronics assembly 200 with the AIMD housing 202, and may be followed by functional testing of the electronics if desired.

Next, the subassembly 204 (the assembled AIMD housing 202 and electronics 200) are positioned relative to a dispenser 206 for placing a dampening layer therein. The dispenser 206 is coupled to a heating/mixing chamber 208, which receives material from one or more hoppers 210, 212. For example, pelletized material for the dampening layer may be in hopper 210, and powdered and/or fibrous filler (ceramic, Zeolite, textile, etc., as described above) may be in hopper 212. Metered amounts of each material can be heated and mixed together in chamber 208 and dispensed via dispenser 206. The dispenser 206 may include a foaming head that receives compressed gas (air, dry air, Nitrogen, Argon, or other constituents as discussed above).

With the dampening layer placed, the filled subassembly 214 can go to a top attach processing step, where another part 216 of the AIMD housing is secured thereto. The result is a hermetically sealed assembly. Functional testing may take place after dampening layer deposition and before top attach, if desired. Cooling, outgassing and/or other processing may also take place after the dampening layer is deposited and before top attach takes place, if desired.

Figure 4:
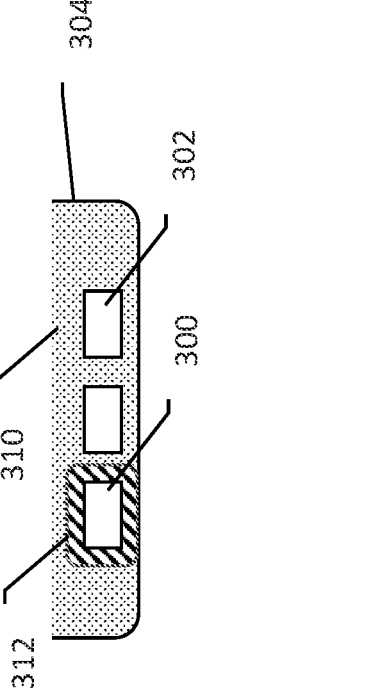
FIG. 4 shows another illustrative example.

FIG. 4 shows another example. Here, several device components 300, 302 are inside of a device housing 304. A dampening layer is shown at 310. One of the components 300 has a separate encapsulant 312 thereabout. The encapsulant 312 may have different density, thermal conductivity, heat capacity, and/or dielectric strength, than the dampening layer, where specific properties of the encapsulant 312 are selected to accommodate the needs of component 300.

In an example, the component 300 may be an inductive element or coil in a rechargeable AIMD adapted to receive and transduce magnetic fields into electric current. The process typically generates heat, and thermal isolation of such a component could increase heating overmuch. To encourage heat dissipation, a more thermally conductive encapsulant region 312 may be used over component 300, while the other components 302 are covered by the dampening layer 310 having reduced thermal conductivity. Layer 312 may be applied separately from dampening layer, or may be applied in the same process step by varying the composition of material it is dispensed in different areas of the device 304. Layer 312 may be, in some examples, an alternative to an approach which uses an air gap around selected componentry.

In an example, layer 312 has a higher thermal conductivity than dampening layer 310, to aid in heat dissipation during use of component 300, for example, if component 300 is used to handle significant power over a relatively longer time period, such as a recharging circuit for an AIMD, where recharging may take place over the course of several minutes (5 to 60 minutes, for example). In an example, layer 312 has a lower thermal conductivity than dampening layer, to limit thermal effects to the component 300, for example. In an example, layer 312 has a higher density than dampening layer 310. In an example, layer 312 has a lower density than dampening layer 310. In an example, layer 312 has a greater heat capacity than dampening layer 310, which may be useful to provide heat sink capability if component 300 is subject to short term, high power operations, such as with a charging circuit of an implantable defibrillator, which may experience large currents (1 ampere or more) for short periods of time (less than 30 seconds). In an example, layer 312 has reduced heat capacity and higher thermal conductivity in combination, allowing quick dissipation of heat.

In still other example, the layer 312 is a more rigid material than other parts of the dampening layer, so as to avoid absorbing mechanical energy such as that generated by an acoustic transducer, or that to be sensed by an accelerometer.

Each of these non-limiting examples can stand on its own, or can be combined in various permutations or combinations with one or more of the other examples. The above detailed description includes references to the accompanying drawings, which form a part of the detailed description. The drawings show, by way of illustration, specific embodiments. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like. For example, such code may take the form of control instructions for an extruder or for a robotic assembly device or system.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, innovative subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the protection should be determined with reference to the appended claims, along with the full scope of equivalents to which such claims are entitled.

What is claimed is:

1. A method of manufacturing an implantable medical device comprising:
   assembling a plurality of electrical components for the implantable medical device; and
   dispensing a dampening layer onto a least a portion of the assembled electrical components, wherein the dampening layer comprises:
      a first material selected from the group consisting of thermoplastic, elastomer, thermoplastic elastomer (TPE), hot melt polymer and blends thereof, the first material having a first heat capacity;
      a second material having a second heat capacity that is less than the first heat capacity, the second material being selected from the group consisting of Zeolites, ceramic, carbon fibers, textile fibers, or entrapped gas;
   wherein the step of dispensing the dampening layer is performed by mixing the first and second materials together, and at least the first material is in a molten state when applied to the assembled electrical components.

2. The method of claim 1, wherein the first material makes up a majority, by volume, of the dampening layer.

3. The method of claim 1, wherein the first material makes up a majority, by mass, of the dampening layer.

4. The method of claim 1, wherein the second material reduces a heat capacity of the dampening layer by at least 10%, relative to a heat capacity of the first material.

5. The method of claim 1, wherein the second material reduces a thermal conductivity of the dampening layer by at least 10%, relative to a thermal conductivity of the first material.

6. The method of claim 1, wherein the second material is entrapped gas, and the step of dispensing the dampening layer is performed by ejecting the first material from a foaming head.

7. The method of claim 1, wherein the first material is provided in a pelletized form, the second material is mixed with the first material as a powder or pelletized form, and the mixed combination of the first and second materials is then heated to melt at least the first material so that the dispensing step can be performed.

8. The method of claim 1, wherein the dampening layer has a density that is reduced by at least 10% relative to a density of the first material.

9. The method of claim 1, further comprising placing the electrical components in a first part of an enclosure for the implantable medical device prior to dispensing the dampening layer thereon.

10. The method of claim 9, further comprising placing a second part of the enclosure after dispensing the dampening layer, and securing the first part and second part of the enclosure to one another.

11. The method of claim 1, wherein the dispensing step is performed by molding the dampening layer onto the portion of the assembled electrical components.

12. The method of claim 1, wherein the second material second material is selected from the group consisting of Zeolites, ceramic, carbon fibers, and textile fibers, and the dispensing step further comprises infusing a gas into a blend of the first and second materials.

13. The method of claim 1, further comprising applying a separate layer of encapsulant having a different thermal conductivity than the dampening layer to at least one electrical component prior to dispensing the dampening layer.

14. The method of claim 1, further comprising applying a separate layer of encapsulant having a different heat capacity than the dampening layer to at least one electrical component prior to dispensing the dampening layer.

* * * * *